US008623329B1

(12) United States Patent
Hansen et al.

(10) Patent No.: US 8,623,329 B1
(45) Date of Patent: Jan. 7, 2014

(54) METHOD FOR THE TREATMENT OF LUNG TUMORS

(75) Inventors: Brian Nils Hansen, Longmont, CO (US); Brooks Michael Hybertson, Boulder, CO (US)

(73) Assignee: Aerophase, Inc., Longmont, CO (US)

( * ) Notice: Subject to any disclaimer, the term of this patent is extended or adjusted under 35 U.S.C. 154(b) by 356 days.

(21) Appl. No.: 12/899,736

(22) Filed: Oct. 7, 2010

Related U.S. Application Data

(60) Provisional application No. 61/251,055, filed on Oct. 13, 2009.

(51) Int. Cl.
*A61K 9/12* (2006.01)
*A61K 31/355* (2006.01)

(52) U.S. Cl.
USPC .......... 424/43; 514/449

(58) Field of Classification Search
USPC .......... 424/43; 514/449
See application file for complete search history.

(56) References Cited

U.S. PATENT DOCUMENTS

| | | | | |
|---|---|---|---|---|
| 7,288,243 | B2 | 10/2007 | Knight | |
| 2003/0181737 | A1* | 9/2003 | Nair | 549/510 |
| 2005/0009783 | A1* | 1/2005 | Kagkadis | 514/58 |
| 2008/0066741 | A1* | 3/2008 | LeMahieu et al. | 128/200.21 |
| 2010/0181387 | A1* | 7/2010 | Zaffaroni et al. | 239/13 |

OTHER PUBLICATIONS

Prasad et al. "alpha-Tocopherol Succinate, the Most Effective Form of Vitamin E for Adjuvant Cancer Treatment: A Review," Journal of the American College of Nutrition, 2003, 22(2), pp. 108-117.*
Derwent English Abstract of CN 101204373 A by Bi, W. and Li, S. which was published on Jun. 25, 2008.*
The Merck Index, 10th edition, Merck & Co., Inc.: Rahway, NJ, 1983, pp. 207-208 (entry 212).*
Sigma-Aldrich Catalog of Fine Chemicals, 2007-2008, pp. 1156-1157.*
Praxair "Carbon Dioxide" pure gases product descriptions accessed on Feb. 12, 2013 at http://www.praxair.com/na/ca/en/can.nsf/0/898C009D26127E02852577BC0061BF8E/$file/Sec+C+-°Page+C-15+and+C-16.pdf.*
Gurusamy Manivannan and Samuel P. Sawan, "The Supercritical State" In Supercritical Fluid Cleaning: Fundamentals, Technology, and Applications, John McHardy and Samuel P. Sawan, eds., Noyes Publications: Westwood, New Jersey, 1998, pp. 1 and 4-6.*
Shirish M. Chitanvis et al., "Dynamics of Particle Removal by Supercritical Carbon Dioxide" In Supercritical Fluid Cleaning: Fundamentals, Technology, and Applications, John McHardy and Samuel P. Sawan, eds., Noyes Publications: Westwood, New Jersey, 1998, pp. 70 and 80.*
Chu, Q.; Vincent, M.; Logan, D.; MacKay, J. A.; Evans, W. K., Taxanes as first-line therapy for advanced non-small cell lung cancer: a systematic review and practice guideline. Lung Cancer, 2005, pp. 355-374, vol. 50, issue 3.

Gagnadoux, F.; Hureaux, J.; Vecellio, L.; Urban, T.; Le Pape, A.; Valo, I.; Montharu, J.; Leblond, V.; Boisdron-Celle, M.; Lerondel, S.; Majoral, C.; Diot, P.; Racineux, J. L.; Lemarie, E., Aerosolized chemotherapy. J Aerosol Med Pulm Drug Deliv, 2008, pp. 61-70, vol. 21, issue 1.
Gautam, A.; Koshkina, N., Paclitaxel (taxol) and taxoid derivates for lung cancer treatment: potential for aerosol delivery. Curr Cancer Drug Targets, 2003, pp. 287-296, vol. 3, issue 4.
Hershey, A. E.; Kurzman, I. D.; Forrest, L. J.; Bohling, C. A.; Stonerook, M.; Placke, M. E.; Imondi, A. R.; Vail, D. M., Inhalation chemotherapy for macroscopic primary or metastatic lung tumors: proof of principle using dogs with spontaneously occurring tumors as a model. Clin Cancer Res, 1999, pp. 2653-2659, vol. 5, issue 9.
Knight, V.; Koshkina, N. V.; Golunski, E.; Roberts, L. E.; Gilbert, B. E., Cyclosporin A aerosol improves the anticancer effect of paclitaxel aerosol in mice. Trans Am Clin Climatol Assoc, 2004, pp. 395-404, vol. 115.
Koshkina, N. V.; Knight, V.; Gilbert, B. E.; Golunski, E.; Roberts, L.; Waldrep, J. C., Improved respiratory delivery of the anticancer drugs, camptothecin and paclitaxel, with 5% CO2-enriched air: pharmacokinetic studies. Cancer Chemother Pharmacol 2001, pp. 451-456, vol. 47, issue 5.
Koshkina, N. V.; Waldrep, J. C.; Roberts, L. E.; Golunski, E.; Melton, S.; Knight, V., Paclitaxel liposome aerosol treatment induces inhibition of pulmonary metastases in murine renal carcinoma model. Clin Cancer Res 2001, pp. 3258-3262, vol. 7, issue 10.
Latimer, P.; Menchaca, M.; Snyder, R. M.; Yu, W.; Gilbert, B. E.; Sanders, B. G.; Kline, K., Aerosol delivery of liposomal formulated paclitaxel and vitamin E analog reduces murine mammary tumor burden and metastases. Exp Biol Med (Maywood), 2009, pp. 1244-1252, vol. 234, issue 10.
Sharma, S.; White, D.; Imondi, A. R.; Placke, M. E.; Vail, D. M.; Kris, M. G., Development of inhalational agents for oncologic use. J Clin Oncol 2001, pp. 1839-1847, vol. 19, issue 6.
Tatsumura, T.; Koyama, S.; Tsujimoto, M.; Kitagawa, M.; Kagamimori, S., Further study of nebulisation chemotherapy, a new chemotherapeutic method in the treatment of lung carcinomas: fundamental and clinical. Br J Cancer 1993, pp. 1146-1149, vol. 68, issue 6.
Zou, Y.; Fu, H.; Ghosh, S.; Farquhar, D.; Klostergaard, J., Antitumor activity of hydrophilic Paclitaxel copolymer prodrug using locoregional delivery in human orthotopic non-small cell lung cancer xenograft models. Clin Cancer Res 2004, pp. 7382-7391, vol. 10, issue 21.

* cited by examiner

*Primary Examiner* — James H. Alstrum-Acevedo

(57) ABSTRACT

The present invention provides a method of inhibiting cancer growth in the lungs of a mammal through the inhalation administration of aerosol particles of an anti-cancer drug formulation. Further, the present invention provides a formulation for aerosol delivery that comprises a combination of paclitaxel, α-tocopheryl succinate; sorbitan trioleate, ethanol, and carbon dioxide. Prior studies have indicated that aerosol administration of cancer drugs holds great potential as a treatment modality, both for lung cancer and for lung metastases of other cancers. Practice of the invention has been demonstrated using a mouse model of lung cancer, in which intrapulmonary deposition of paclitaxel by aerosol inhalation reduced lung tumor size and increased body weight in tumor-bearing mice.

14 Claims, 3 Drawing Sheets

METHOD FOR THE TREATMENT OF LUNG TUMORS

STATEMENT REGARDING FEDERALLY SPONSORED RESEARCH AND DEVELOPMENT

This invention was made with Government support under grant R44CA096409 awarded by the US National Cancer Institute, National Institutes of Health. The Government has certain rights in the invention.

CROSS-REFERENCE TO RELATED APPLICATIONS

Not applicable.

BACKGROUND

Field of Invention

This invention relates to a process for treating primary or metastatic lung tumors by inhalation of the anticancer drug paclitaxel in an aerosol formulation comprising paclitaxel along with α-tocopheryl succinate, sorbitan trioleate, and ethanol as solubility enhancers, and carbon dioxide as solvent.

Lung cancer is the leading cause of cancer deaths in the U.S. and other developed countries, and there remains a great need for improvements in its prevention, detection, and treatment. Tobacco use is the predominant risk factor for lung cancer, with about 87% of lung cancer cases linked to cigarette smoking (3), making smoking cessation an essential part of reducing the personal and societal impacts lung cancer (5). However, even if dramatic reductions in smoking were achieved, there would still remain a crucial need for improved forms of lung cancer treatment. Surgery remains a primary focus of therapy, but a prominent role for chemotherapy has grown over the past decade, with demonstrated survival benefits demonstrated for a variety of chemotherapeutic approaches (2, 17). It is expected that continued advances in early detection technologies will further increase the importance of chemotherapy in lung cancers (9). Furthermore, about half of lung cancer patients develop lung tumor recurrence or develop secondary tumors after surgical resection of early-stage lung cancer tumors (23), making concurrent chemotherapy a critical component of treatment. Unfortunately, the therapeutic results of chemotherapy in treating lung cancer have been hindered by the inability to achieve therapeutic drug concentrations at the site of the tumor, raising interest in targeted forms of administration (18). The good news is that lung cancer may in fact be the easiest form of cancer to treat with a targeted delivery approach, given that pharmaceutical aerosols can directly reach the affected sites with some forms of lung cancer.

In the US, aerosol drug delivery is a mainstay for treatment of lung illnesses such as asthma and is making inroads into the treatment of other diseases such as cystic fibrosis. Aerosol delivery of anticancer drugs to the lungs is an intriguing prospect, but its potential is severely limited by the nebulizer systems that are currently available. Many chemotherapeutic agents such as as paclitaxel, taxotere, etoposide, topotecan, and camptothecin have very low solubility in aqueous solutions. Current nebulizers and spray systems require water-soluble formulations. Aerophase has developed an aerosol drug-delivery method that should overcome these limitations based on the use of supercritical $CO_2$ as the solvent and propellant for aerosol generation. The use of $CO_2$ solves the problem that aqueous nebulizers have with aerosolizing lipophilic drugs.

Carbon dioxide propellant aerosol systems may be advantageous for lung cancer aerosol therapy because $CO_2$ stimulates deep breathing. Increased respiratory tract deposition of inhaled aerosol particles of anticancer drugs has previously been demonstrated for 5% $CO_2$-enriched air (48). As taught by Waldrep, et al., in U.S. Pat. No. 6,440,393, carbon dioxide gas can be mixed with air and then an aqueous drug solution or suspension can be aerosolized in said $CO_2$-air mixture. The present invention is clearly distinct from U.S. Pat. No. 6,440,393, and has the advantage that $CO_2$ is already present in the drug solution and drug aerosol product, and does not need to be added separately, only diluted to an appropriate inhalation level with air or oxygen.

In addition to lipophilic drug capability, a significant advantage of the $CO_2$ propellant aerosol systems for lung cancer therapy is aerosol size and range. The high pressure and high energy released in the $CO_2$ expansion ensure the formation of small aerosols. The optimal aerosol size for effective lung deposition is around 1 μm. The $CO_2$ aerosol generation system described in the present invention has significant flexibility in adjusting aerosol size around 1 μm with pressure, composition, and mechanical configuration.

Due to the high reactivity and toxicity of chemotherapeutic agents, and interest in targeted delivery, many scientists and clinicians have noted that aerosol delivery of anticancer drugs by inhalation directly to the lung epithelium appears to be highly desirable (18, 21). In fact, aerosol administration has been gaining in interest for oncologic use and has been examined as a way to get interferon-γ, interleukin-2, tocopherol succinate, granulocyte-macrophage colony-stimulating factor (GM-CSF), 13-cis-retinoic acid, paclitaxel, and 9-nitro-camptothecin into the lungs (1, 4, 10-13, 18, 19, 21, 22, 24). In a review article published in 2003, it was noted for paclitaxel (PTX):

"The potential of inhaled PTX therapy is just beginning to be grasped. It is likely that the inhalation studies of PTX and other anticancer agents will increase dramatically both because of the ease of drug delivery and its ability to permit lung targeting. To accomplish this, several challenges need to be overcome, including optimization of delivery formulations . . . (8)"

Aerosol delivery of pharmaceuticals is a fast-growing field, but no approved aerosol therapies are available for the treatment of lung cancer. Many of the agents that can act as cancer cell growth inhibitors are highly lipophilic and cannot readily be delivered to the lungs with traditional aerosol methods—most of which rely on the water solubility of the drugs. The goals of this project are to develop marketable instrumentation and aerosol methodology to safely and practically administer chemotherapeutic agents directly to the pulmonary epithelium using supercritical $CO_2$. The instrumentation will be designed to be simple to use for aerosol delivery of anticancer agents such as paclitaxel, taxotere, etoposide, topotecan, and camptothecin, which are currently FDA-approved for injection delivery. The aerosol delivery of lipophilic antineoplastics will create a local high concentration of the chemotherapeutic agent for targeted delivery to the lungs with less systemic stress (18). An improved method for aerosol delivery of anticancer agents to the lungs may significantly reduce mortality from lung cancer. The reasons for using intrapulmonary aerosol deposition as the drug delivery method include 1) increased efficacy of drug, 2) decreased systemic absorption and concomitant side effects, and 3) increased local concentration of drug at the site of the tumor cells. Our primary motive for pursuing supercritical fluid aerosol delivery of chemotherapeutic pharmaceuticals is for more efficient and selective deposition of the agent. This method will almost certainly allow deposition of lipophilic anticancer drugs in the more distal parts of the lungs than is possible with other aerosol delivery systems.

The present invention pertains to aerosol paclitaxel delivery for treatment and/or prevention of primary or metastatic cancer in the lungs using a formulation of paclitaxel, tocopheryl succinate, sorbitan trioleate, ethanol, and carbon dioxide. This combination demonstrated beneficial results in a mouse model of lung cancer.

α-Tocopheryl succinate (αTS) is a vitamin E analogue that helps to solubilize paclitaxel in supercritical carbon dioxide and that has gained extensive interest in recent years for its possible use in combination with other chemotherapeutic agents (25). In the present invention, αTS is included in the aerosol paclitaxel formulation to improve solubility and effectiveness for lung cancer treatment.

Sorbitan trioleate (SPAN 85) is a lipid-soluble nonionic surfactant used in the present invention to increase the solubility of paclitaxel in supercritical carbon dioxide.

Ethanol is used in the present invention as a cosolvent to increase the solubility of paclitaxel in supercritical carbon dioxide.

Supercritical carbon dioxide is used in the present invention as a solvent and propellant to dissolve the paclitaxel and surfactant/cosolvent mixture and form a spray to generate respirable aerosols of paclitaxel.

In one embodiment, the pressure of the formulation is maintained between 900 and 5000 psi prior to spraying the formulation through a valve into a region of ambient atmospheric pressure for inhalation administration.

The present invention also includes the capability of adding additional active agents to the inhaled formulation:

Some lung tumors exhibit resistance to drugs including paclitaxel. A variety of mechanisms may be involved, including tubulin-related mutations and multidrug resistance gene upregulation. In the case of drug resistance, agents can be added to interfere with the expression and activity of P-glycoprotein transport of paclitaxel out of the targeted cells. In other words, in addition to the paclitaxel, the formulation can include active agents to decrease drug resistance to paclitaxel. For example, the formulation can include cyclosporin, Other lung cancer drugs can be utilized in the supercritical fluid formulation in addition to or in the place of paclitaxel. This would include, but not be limited to, other taxanes such as docetaxel, topoisomerase inhibitors such as etoposide, camptothecin, or doxorubicin, DNA crosslinking agents such as cisplatin, and other agents active against lung tumors.

Sievers, Hybertson, and Hansen initially studied supercritical fluid carbon dioxide as a solvent to generate small aerosols of pharmaceuticals to be directly inhaled because the particle size was easy to control. Coincidentally, carbon dioxide is also a practical respiratory stimulant along with its role as an aerosol generating propellant in the present pulmonary aerosol delivery device.

Aerosol drug inhalation is an ancient practice that extends back to as long as people have intentionally inhaled smoke, but more recently it has been suggested as a particularly attractive route for the prevention or treatment of lung cancer (4-6, 16, 18, 20). It has been considered to be one of the research priorities for the future lung cancer chemoprevention. Other potential anti-neoplastic agents, such as liposomal interleukin-2, liposomal interferon-γ, vitamin A, paclitaxel, 9-nitrocamptothecin, 5-fluorouracil, and doxorubicin (91) have been studied for possible aerosol inhalation delivery to patients with lung cancer (7, 10, 12-15, 21, 22). The advantages of this approach include reducing or preventing systemic toxicities due to directly targeting pulmonary tissue.

The most common types of aerosol generators used in aerosol medicine are dry powder inhalers, nebulizers, and pressurized metered dose inhalers. The dry powder inhaler (DPI) is breath activated using the inhaled air to move a dry powder into the lungs. Formulation of drugs for this type of inhaler is particularly difficult because most pharmaceuticals stick together and form large particles that can't be inhaled. Nebulizers work on the Bernoulli effect using compressed air to draw the liquid solution up a tube and the shearing energy of the air to break the liquid into small droplets. The metered dose inhaler (MDI) uses drugs dissolved or suspended in freons. Aerosols are generated by both the gas expansion energy and solvent evaporation. In the present invention, the aerosol generation occurs by expansion of a supercritical carbon dioxide solution formulation, which has higher aerosolization energy than the other aerosol methods, which allows very fine aerosol formation which can reach the upper airways and the distal parts of the lungs.

Advantages

Accordingly one or more embodiments of the present invention may have one or more of the following advantages:

It is an advantage of the invention to provide a method for treating lung cancer that with paclitaxel that allows much lower amounts of paclitaxel to be used, due to its targeted delivery to the lungs.

BRIEF DESCRIPTION OF THE DRAWINGS

The Detailed Description and Examples should be viewed together with the Drawings in which:

FIG. 2 shows mean body weight of mice as described in Example 1; and

FIG. 3 shows mean tumor volume as described in Example 1.

DETAILED DESCRIPTION OF THE INVENTION

Figure 1:
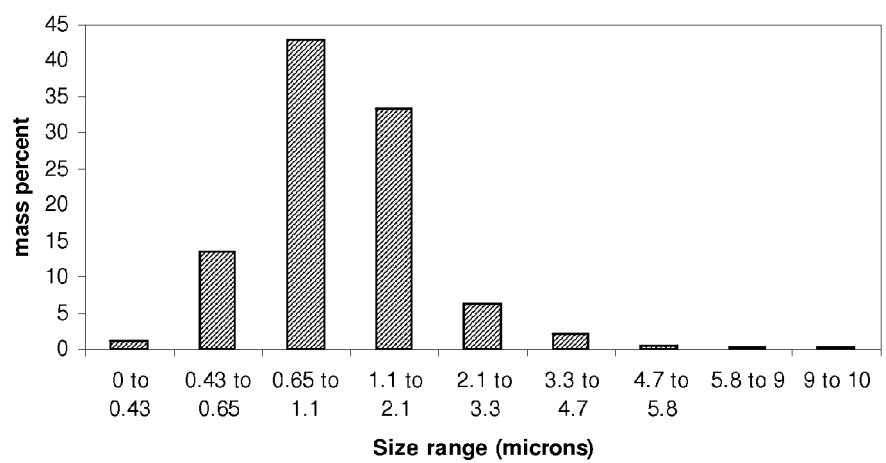
FIG. 1 shows particle size distribution after collection of an aerosol as described in Example 1.

One of ordinary skill in the art will be able to envision and practice the invention as described or in related, alternative embodiments.

In one embodiment, the invented formulation comprises 60 mg paclitaxel, 0.3 g α-tocopheryl succinate (αTS), 0.66 g sorbitan trioleate (SPAN85), 5.8 g ethanol (EtOH), and 230 g of $CO_2$ enclosed in a 48 ci pressure vessel, then pressurized to 1600 psig with helium gas.

Broadly, the invented lung cancer therapeutic formulation includes paclitaxel, solubility enhancing agents αTS, SPAN85, and EtOH, and carbon dioxide as the solvent and propellant.

The ratios of paclitaxel to the solubility enhancing agents and pressurized solvent is not firmly fixed, but can be varied. By mass, the formulation can be described as

TABLE 1

| Relative mass | Formulation component |
|---|---|
| 1 | paclitaxel |
| 5 | α-tocopheryl succinate (αTS) |
| 11 | sorbitan trioleate (SPAN85) |
| 97 | ethanol (EtOH) |
| 3833 | $CO_2$ |

As noted, these relative ratios are not fixed, but can be adjusted to meet the paclitaxel delivery needs. For example, for a given amount of paclitaxel the relative amounts of the solubility enhancing agents αTS, SPAN85, and ethanol can be adjusted, as well as the amount of carbon dioxide solvent needed to dissolve the resultant mixture. In such a case, one of many permutations would be that the use of additional SPAN85 could decrease the amount of αTS needed in the formulation. Depending on the desired amount of paclitaxel delivered, the formulation can include, minimally, paclitaxel and carbon dioxide alone. Therefore, the invention description can be described as ranges of concentrations used to create a suitable paclitaxel formulation for aerosol delivery, as low as zero for individual solubility enhancing agents depending on the amounts used of the others, and a range of carbon dioxide solvent for dissolving the resultant paclitaxel-containing mixture:

TABLE 2

| Formulation component | Relative mass range |
|---|---|
| paclitaxel | 1 |
| α-tocopheryl succinate (αTS) | 0 to 100 |
| sorbitan trioleate (SPAN85) | 0 to 200 |
| ethanol (EtOH) | 0 to 2000 |
| $CO_2$ | 100 to 10000 |

In other embodiments, other agents are added to improve the formulation effectiveness against lung tumors that exhibit resistance to paclitaxel. A variety of mechanisms may be involved. In the case of multidrug resistance gene upregulation, agents can be added to interfere with the expression and activity of P-glycoprotein transport of paclitaxel out of the targeted cells. In other words, in addition to the paclitaxel, the formulation can include active agents to decrease drug resistance to paclitaxel. For example, the formulation can include cyclosporin, quinidine, biricodar, or other agents to decrease paclitaxel efflux from tumor cells.

Other lung cancer drugs can be utilized in the supercritical fluid formulation in addition to paclitaxel. This would include, but not be limited to, other taxanes such as docetaxel, topoisomerase inhibitors such as etoposide, camptothecin, or doxorubicin, DNA crosslinking agents such as cisplatin, and other agents active against lung tumors.

DETAILED DESCRIPTION

Examples

Example 1

We demonstrated the use of an aerosol formulation of 60 mg paclitaxel, 0.3 g αTS, 0.66 g SPAN85, 5.8 g EtOH, and 230 g of $CO_2$, pressurized to 1600 psi with helium gas headspace and released through a high pressure nozzle to form respirable, airborne paclitaxel aerosol particles, deposit relevant doses in mouse lungs, and inhibit lung tumor growth in a mouse model of nonsmall cell lung cancer.

FIG. 1 shows the particle size distribution after collection of said paclitaxel aerosol on Anderson cascade impactor and quantitative analysis of paclitaxel on the stages by HPLC-MS/MS. The mass median aerodynamic diameter is 1.2 μm which is ideal for particle inhalation:

Aerosol delivery of the paclitaxel formulation to mice gave a per-mouse, lung-specific dose of 30±5 ng paclitaxel, an amount calculated to be appropriate for further study in a lung tumor model.

A mouse model of lung cancer was used for further testing of the paclitaxel aerosol formulation. Briefly, athymic nude mice were injected with human nonsmall cell lung cancer A549 cell line cell stably transfected with the firefly luciferase gene (A549-luc cells). On day 12, mice verified to have lung tumor formation in vivo by luciferin-dependent chemiluminescence were divided into two groups, one untreated control tumor group and one aerosol-treated tumor group, receiving 30 ng of paclitaxel by inhalation of the aforementioned aerosol formulation 3× per week, with monitoring of body weights. At day 33, the experiment was ended, body weights assessed and excised lung tumor volumes measured.

Figure 2:
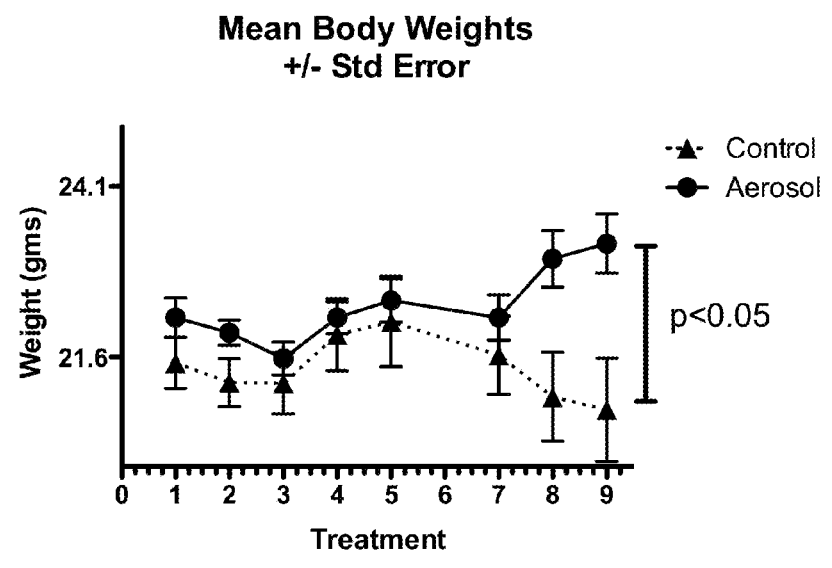

It was determined that tumor-bearing mice treated by inhalation of the paclitaxel aerosol formulation gained weight, but untreated tumor-bearing mice lost weight, an indication that the overall health of the treated mice was better than that of the untreated mice. The mean body weight was higher in the paclitaxel aerosol-treated mice than the untreated mice at day 31 after A549 lung tumor cell injection ($p<0.05$) as shown in FIG. 2.

Figure 3:
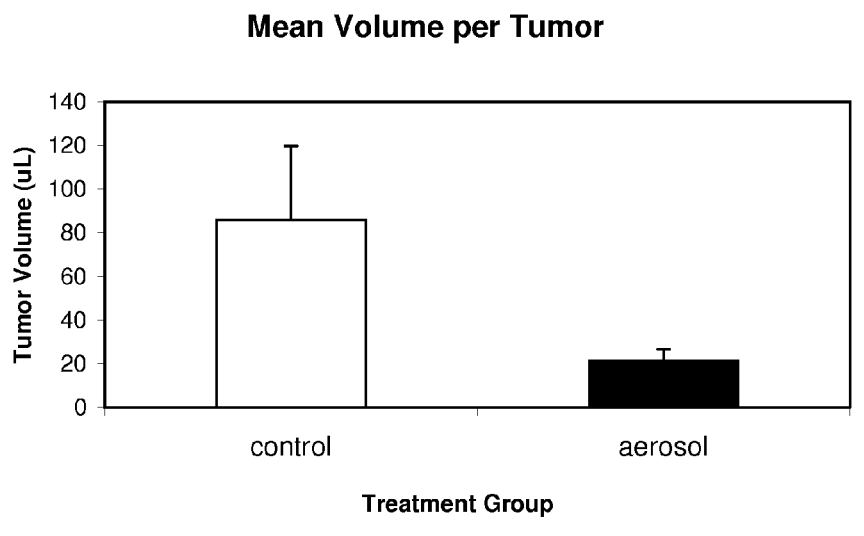

Notably, there was also a decrease in lung tumor volume in the mice treated with inhaled paclitaxel aerosol formulation compared to the untreated mice. The total number of lung tumors per mouse was not different between the two groups, but the lung tumor volume was significantly lower in the mice that were treated with the inhaled paclitaxel aerosol formulation ($p<0.05$), as shown in FIG. 3.

CITED REFERENCES

1. Anderson P M, Markovic S N, Sloan J A, Clawson M L, Wylam M, Arndt C A, Smithson W A, Burch P, Gornet M, and Rahman E. Aerosol granulocyte macrophage-colony stimulating factor: a low toxicity, lung-specific biological therapy in patients with lung metastases. *Clin Cancer Res* 5: 2316-2323., 1999.
2. Berhoune M, Banu E, Scotte F, Prognon P, Oudard S, and Bonan B. Therapeutic strategy for treatment of metastatic non-small cell lung cancer. *Ann Pharmacother* 42: 1640-1652, 2008.
3. Cohen V and Khuri F R. Progress in lung cancer chemoprevention. *Cancer Control* 10: 315-324., 2003.
4. Dahl A R, Grossi I M, Houchens D P, Scovell L J, Placke M E, Imondi A R, Stoner G D, De Luca L M, Wang D, and Mulshine J L. Inhaled isotretinoin (13-cis retinoic acid) is an effective lung cancer chemopreventive agent in A/J mice at low doses: a pilot study. *Clin Cancer Res* 6: 3015-3024., 2000.
5. Dragnev K H, Stover D, and Dmitrovsky E. Lung cancer prevention: the guidelines. *Chest* 123: 60S-71S., 2003.
6. Gagnadoux F, Hureaux J, Vecellio L, Urban T, Le Pape A, Valo I, Montharu J, Leblond V, Boisdron-Celle M, Lerondel S, Majoral C, Diot P, Racineux J L, and Lemarie E. Aerosolized chemotherapy. *J Aerosol Med Pulm Drug Deliv* 21:61-70, 2008.
7. Gautam A, Densmore C L, Melton S, Golunski E, and Waldrep J C. Aerosol delivery of PEI-p53 complexes inhibits B16-F10 lung metastases through regulation of angiogenesis. *Cancer Gene Ther* 9: 28-36., 2002.
8. Gautam A and Koshkina N. Paclitaxel (taxol) and taxoid derivates for lung cancer treatment: potential for aerosol delivery. *Curr Cancer Drug Targets* 3: 287-296, 2003.
9. Greenberg A K and Lee M S. Biomarkers for lung cancer: clinical uses. *Curr Opin Pulm Med* 13: 249-255, 2007.
10. Halme M, Maasilta P, Repo H, Ristola M, Taskinen E, Mattson K, and Cantell K. Inhaled recombinant interferon gamma in patients with lung cancer: pharmacokinetics and effects on chemiluminescence responses of alveolar macrophages and peripheral blood neutrophils and monocytes. *Int J Radiat Oncol Biol Phys* 31: 93-101, 1995.
11. Hershey A E, Kurzman I D, Forrest L J, Bohling C A, Stonerook M, Placke M E, Imondi A R, and Vail D M. Inhalation chemotherapy for macroscopic primary or metastatic lung tumors: proof of principle using dogs with spontaneously occurring tumors as a model. *Clin Cancer Res* 5: 2653-2659., 1999.
12. Kessler R, Dumont S, Bartholeyns J, Weitzenblum E, and Poindron P. Antitumoral potential of aerosolized interferon-gamma in mice bearing lung metastases. *Am J Respir Cell Mol Biol* 10: 202-206, 1994.
13. Khanna C, Anderson P M, Hasz D E, Katsanis E, Neville M, and Klausner J S. Interleukin-2 liposome inhalation therapy is safe and effective for dogs with spontaneous pulmonary metastases. *Cancer* 79: 1409-1421, 1997.
14. Knight V, Koshkina N, Waldrep C, Giovanella B C, Kleinerman E, and Gilbert B. Anti-cancer activity of 9-nitrocamptothecin liposome aerosol in mice. *Trans Am Clin Climatol Assoc* 111: 135-145, 2000.
15. Kohlhaufl M, Haussinger K, Stanzel F, Markus A, Tritschler J, Muhlhofer A, Morresi-Hauf A, Golly I, Scheuch G, Jany B H, and Biesalski H K. Inhalation of aerosolized vitamin a: reversibility of metaplasia and dysplasia of human respiratory epithelia—a prospective pilot study. *Eur J Med Res* 7: 72-78., 2002.
16. Koshkina N V, Knight V, Gilbert B E, Golunski E, Roberts L, and Waldrep J C. Improved respiratory delivery of the anticancer drugs, camptothecin and paclitaxel, with 5% CO2-enriched air: pharmacokinetic studies. *Cancer Chemother Pharmacol* 47: 451-456., 2001.
17. Lilenbaum R C. New horizons in chemotherapy: platforms for combinations in first-line advanced non-small cell lung cancer. *J Thorac Oncol* 3: S171-174, 2008.
18. Sharma S, White D, Imondi A R, Placke M E, Vail D M, and Kris M G. Development of inhalational agents for oncologic use. *J Clin Oncol* 19: 1839-1847., 2001.
19. Skubitz K M and Anderson P M. Inhalational interleukin-2 liposomes for pulmonary metastases: a phase I clinical trial. *Anticancer Drugs* 11: 555-563., 2000.
20. Spinella M J and Dmitrovsky E. Aerosolized delivery and lung cancer prevention: pre-clinical models show promise. *Clin Cancer Res* 6: 2963-2964, 2000.
21. Tatsumura T, Koyama S, Tsujimoto M, Kitagawa M, and Kagamimori S. Further study of nebulisation chemotherapy, a new chemotherapeutic method in the treatment of lung carcinomas: fundamental and clinical. *Br J Cancer* 68: 1146-1149, 1993.
22. Verschraegen C F, Gilbert B E, Huaringa A J, Newman R, Harris N, Leyva F J, Keus L, Campbell K, Nelson-Taylor T, and Knight V. Feasibility, phase I, and pharmacological study of aerosolized liposomal 9-nitro-20(S)-camptothecin in patients with advanced malignancies in the lungs. *Ann N Y Acad Sci* 922: 352-354, 2000.
23. Walsh G L, Pisters K M, and Stevens C. Treatment of stage I lung cancer. *Chest Surg Clin N Am* 11: 17-38, vii., 2001.
24. Wang D L, Marko M, Dahl A R, Engelke K S, Placke M E, Imondi A R, Mulshine J L, and De Luca L M. Topical delivery of 13-cis-retinoic acid by inhalation up-regulates expression of rodent lung but not liver retinoic acid receptors. *Clin Cancer Res* 6: 3636-3645., 2000.
25. Zhao Y, Neuzil J, and Wu K. Vitamin E analogues as mitochondria-targeting compounds: from the bench to the bedside? *Mol Nutr Food Res* 53: 129-139, 2009.

We claim:

1. A method of inhibiting cancer growth in the lungs of a mammal comprising inhalation administration of aerosol particles of a pharmaceutical formulation of an anti-cancer drug comprising paclitaxel, α-tocopheryl succinate, sorbitan trioleate, ethanol, and carbon dioxide, wherein the pressure of the formulation is maintained between 900 and 5000 psi prior to spraying the formulation through a valve into a region of ambient atmospheric pressure for inhalation administration.

2. The method according to claim 1 wherein the formulation comprises, per one part by weight of paclitaxel, up to 100 parts by weight α-tocopheryl succinate, up to 200 parts by weight sorbitan trioleate, up to 2000 parts by weight ethanol, and from 100 to 10,000 parts by weight carbon dioxide.

3. The method according to claim 1 wherein the formulation relative mass amounts of paclitaxel, α-tocopheryl succinate, sorbitan trioleate, ethanol, and carbon dioxide are approximately 1:5:11:97:3833, respectively.

4. The method according to claim 1 wherein the aerosol of the formulation is diluted with air prior to inhalation to decrease the carbon dioxide level to 0.1 to 10% of the mixture to be inhaled.

5. The method according to claim 1 in which said mammal is given one or more inhalation exposures to said aerosol.

6. The method according to claim 1 in which said cancer is nonsmall cell lung cancer, bronchioloalveolar carcinoma, or metastatic tumors in the lung.

7. The method of claim 1, wherein said cancer is nonsmall cell lung cancer.

8. The method of claim 1, wherein said cancer is bronchioloalveolar carcinoma.

9. The method of claim 1, wherein the pharmaceutical formulation consists of paclitaxel, α-tocopheryl succinate, sorbitan trioleate, ethanol, and carbon dioxide.

10. A method of treating primary or metastatic lung tumors in a mammal, comprising spraying a pressurized formulation comprising a combination of paclitaxel, α-tocopheryl succinate, sorbitan trioleate, ethanol, and supercritical carbon dioxide from a high pressure vessel in which the formulation pressure is maintained between 900 and 5000 psi into an atmospheric pressure region to form an airborne aerosol mixture that is subsequently inhaled by said mammal.

11. The method according to claim 10 wherein the formulation comprises, per one part by weight of paclitaxel, up to 100 parts by weight α-tocopheryl succinate, up to 200 parts by weight sorbitan trioleate, up to 2000 parts by weight ethanol, and from 100 to 10,000 parts by weight carbon dioxide.

12. The method according to claim 10 wherein the airborne aerosol is diluted with air prior to inhalation to decrease the carbon dioxide level to 0.1 to 10% of the mixture to be inhaled.

13. The method according to claim 10 further comprising repetition of said treatment to result in a total of 3 aerosol inhalation exposures per week.

14. The method of claim 10, wherein the pharmaceutical formulation consists of paclitaxel, α-tocopheryl succinate, sorbitan trioleate, ethanol, and carbon dioxide.

* * * * *